United States Patent
Blanchard

(10) Patent No.: US 6,572,578 B1
(45) Date of Patent: Jun. 3, 2003

(54) FLUID-JET CATHETER AND ITS APPLICATION TO FLEXIBLE ENDOSCOPY

(76) Inventor: Patrick A. Blanchard, 701 Country Club Cir., Building B, Wamego, KS (US) 66547-1146

( * ) Notice: Subject to any disclaimer, the term of this patent is extended or adjusted under 35 U.S.C. 154(b) by 42 days.

(21) Appl. No.: 09/645,502

(22) Filed: Aug. 25, 2000

(51) Int. Cl.[7] .............................................. A61B 17/20
(52) U.S. Cl. ......................... 604/22; 604/43; 606/159
(58) Field of Search .......................... 604/22, 35, 43, 604/44, 27, 147; 606/159, 170

(56) References Cited

U.S. PATENT DOCUMENTS

| | | | |
|---|---|---|---|
| 4,685,472 A | 8/1987 | Muto | |
| 4,913,698 A | 4/1990 | Ito et al. | |
| 4,926,877 A | 5/1990 | Bookwalter | |
| 5,154,724 A | 10/1992 | Andrews | |
| 5,279,542 A | 1/1994 | Wilk | |
| 5,370,609 A | 12/1994 | Drasler et al. | |
| 5,373,854 A | 12/1994 | Kolozsi | |
| 5,496,267 A * | 3/1996 | Drasler et al. | 604/22 |
| 5,562,640 A | 10/1996 | McCabe et al. | |
| 5,573,008 A | 11/1996 | Robinson et al. | |
| 5,630,795 A * | 5/1997 | Kuramoto et al. | 604/30 |
| 5,762,069 A | 6/1998 | Kelleher et al. | |
| 5,766,194 A | 6/1998 | Smith | |
| 5,782,795 A | 7/1998 | Bays | |
| 5,782,848 A * | 7/1998 | Lennox | 606/159 |
| 5,788,667 A * | 8/1998 | Stoller | 606/170 |
| 5,792,166 A | 8/1998 | Gordon et al. | |
| 5,795,308 A | 8/1998 | Russin | |
| 5,807,276 A | 9/1998 | Russin | |
| 5,827,305 A | 10/1998 | Gordon | |
| 5,843,022 A * | 12/1998 | Willard et al. | 604/30 |
| 5,846,219 A | 12/1998 | Vancaillie | |
| 5,871,453 A | 2/1999 | Banik et al. | |
| 5,871,462 A | 2/1999 | Yoder et al. | |
| 5,882,316 A | 3/1999 | Chu et al. | |
| 5,897,507 A | 4/1999 | Kortenbach et al. | |
| 5,910,121 A | 6/1999 | Paolo et al. | |
| 5,928,163 A | 7/1999 | Roberts et al. | |
| 5,928,218 A | 7/1999 | Gelbfish | |
| 5,938,672 A * | 8/1999 | Nash | 606/159 |
| 5,944,686 A | 8/1999 | Patterson et al. | |
| 5,980,468 A | 11/1999 | Zimmon | |
| 5,989,271 A | 11/1999 | Bonnette et al. | |
| 6,007,497 A | 12/1999 | Huitema | |
| 6,053,877 A | 4/2000 | Banik et al. | |
| 6,165,188 A * | 12/2000 | Saadat et al. | 606/159 |
| 6,216,573 B1 * | 4/2001 | Moutafis et al. | 606/167 |
| 6,258,061 B1 * | 7/2001 | Drasler et al. | 604/131 |
| 6,423,027 B1 * | 7/2002 | Gonon | 604/27 |

OTHER PUBLICATIONS

Casale et al., *"Plunging Biopsy": A New Aimed Bioptic Technique*, Endoscopy, vol. 9, 1977: pp. 152–153.

(List continued on next page.)

*Primary Examiner*—Chen Wen Jiang
(74) *Attorney, Agent, or Firm*—James Creighton Wray; Meera P. Narasimhan

(57) ABSTRACT

Fluid jet tubes having operative openings and cell traps for cell cluster, tissue and debris harvesting and collecting are used with an endoscope such that the fluid jets draw-in, stabilize and hold in-vivo target specimens at a distal end. While the catheter grips the tissue by suction, blasts of high pressure solution strip from the tissue and suspend clusters of cells which are ready for analysis. The clusters are entrained in the solution and are recovered in a cell collection trap at the proximal end. Traps are removed, replaced or rotated out of and into alignment with a trap connector to accommodate new target specimens. A switch controls fluid flow, intensity and frequency of fluid jet blasts of the solution. The fluid jet catheter paired with a fiber optic system in an endoscope allows viewing of areas surrounding the distal end of the catheter.

44 Claims, 3 Drawing Sheets

OTHER PUBLICATIONS

Guido et al., *Pipelle Endometrial Sampling: Sensitivity in the Detection of Endometrial Cancer*, Journal of Reproductive Medicine, vol. 40, No. 8, Aug. 1995: pp. 553–555.

Yang et al., *Compact Cell Blocks: Use for Body Fluids, Fine Needle Aspirations, and Endometrial Brush Biopsies*, Acta Cytologica, vol. 42, No. 3, May–Jun. 1998: pp. 703–706.

Rubin et al.; *A Simplified Technique Using Chymotrypsin Lavage for the Cytological Diagnosis of Gastric Cancer*; Cancer, vol. 8, Nov.–Dec. 1955: 1137–1141.

Thabet et al.; *Millipore Filtration Technic for Colon Washings*; American Journal of Clinical Pathology, vol. 34. No. 2, Aug. 1960: 185–188.

Britsch, *A New Method Using a Double Lumen Tube to Obtain Esophageal and Gastric Washings for Cytological Studies*; Acta Cytologica, vol. 6, No. 4; Jun. Aug. 1962: 332–334.

Saburi et al., *A Selective Proteolytic Lavage Method for the Cytodiagnosis of Early Gastric Cancer*; Acta Cytologica, vol. 11, No. 6; Nov.–Dec. 1967:473–476.

Seifert et al., *Gastric Polypectomy*; American Journal of Gastroenterology, vol. 63, No. 6; 1975: 451–456.

Mangla et al., *A New Technique of Endoscopic Biopsy Using Multipurpose Biopsy Tube in the Diagnosis of Reflux Esophagitis*, Digestive Diseases, vol. 20, No. 8; Aug. 1975: 775–780.

Rosenberg et al., *Cell viability studies on the exfoliated colonic cancer cell*, British Journal of Surgery, vol. 65; 1978: 188–190.

Graham et al., *Endoscopic small bowel biopsy in children with a modified multipurpose biopsy tube*, Gastrointestinal Endoscopy, vol. 26, No. 2, 1980:36–37.

Ou Tim et al., *A Suction–Abrasive Cytology Tube for the Diagnosis of Esophageal Carcinoma*, Cancer, vol. 50, No. 4, 1982:782–784.

Batra et al., *Evaluation of brush rinsings for the cytologic diagnosis of esophageal and gastric cancer*, Gastrointestinal Endoscopy, vol. 28, No. 1, 1982: 23–25.

Mortensen et al., *Direct vision brush cytology with colonscopy: an aid to the accurate diagnosis of colonic strictures*, British Journal of Surgery, vol. 71, Dec. 1984:930–932.

Mee et al., *Small bowel biopsy for malabsorption: comparison of the diagnostic adequacy of endoscopic forceps and capsule biopsy specimens*, British Medical Journal, vol. 291, Sep. 21, 1985:769–772.

Achkar et al., *Comparison of suction capsule and endoscopic biopsy of small bowel mucosa*, Gastrointestinal Endoscopy, vol. 32, No. 4, 1986:278–281.

Jeevanandam et al., *A comparison of direct brush cytology and biopsy in the diagnosis of colorectal cancer*, Gastrointestinal Endoscopy, vol. 33, No. 5, 1987:370–371.

Milsom et al., *A suction retriever to expedite recovery of colonic polyps*, Dis Colon Rectum, vol. 30, No. 8, Aug. 1987:644–646.

Waye, *Techniques of Polypectomy: Hot Biopsy Forceps and Snare Polypectomy*, American Journal of Gastroenterology, vol. 82, No. 7, Jul. 1987:615–617.

Bhasin et al., *Endoscopic Suction Cytology in Upper Gastrointestinal Tract Malignancy*, Acta Cytologica, vol. 32, No. 4, Jul.–Aug. 1988:452–454.

Gordon et al., *Cytological Detection of Colorectal Cancer After Administration of Oral Lavage Solution*, Cancer, vol. 68, No. 1, Jul. 1991:106–110.

Gottrand et al., *Comparison of Fiberendoscopy and Watson Capsule for small intestinal biopsy in Infants and Children*, Acta Paediatr, vol. 81, 1992: 399–401.

Rosman et al., *Diagnosis of Colon Cancer by Lavage Cytology with an Orally Administered Balanced Electrolyte Solution*, The American Journal of Gastroenterology, vol. 89, No. 1, 1994 51–56.

McAfee et al., *Tiny snares prove safe and effective for removal of diminutive colorectal polyps*, Gastrointestinal Endoscopy, vol. 40, No. 6, 1994: 301–303.

Ma Eltumi et al., *A comparison of endoscopic and capsule small intestinal biopsy techniques in children with upper gastrointestinal disorders*, Journal of Paediatr. Child Health vol. 32, 1996: 255–256.

Swain, *What Endoscopic Accessories Do We Really Need?* Emerging Technologies in Gastrointestinal Endoscopy, vol. 7, No. 2, Apr. 1997: 313–330.

Iishi et al. *Endoscopic Resection of Large Sessile Colorectal Polyps using a Submucosal Saline Injection Technique*, Hepato–Gastroenterology, vol. 44, 1997: 698–702.

Farouk et al., *Feasibility Study for Use of Brush Cytology as a Complementary Method for Diagnosis of Rectal Cancer*, Dis Colon Rectum, vol. 40, No. 5, May 1997: 609–613.

Roesch, *Polypen und Polyposis*, (In German/English Summary), Forteschritte der Medizin, vol. 115, No. 15, 1997:20–25.

Branski et al., *Histologic Evaluation of Endoscopic Versus Suction Biopsies of Small Intestinal Mucosae in Children with and without Celiac Disease*, Journal of Pediatric Gastroenterology and Nutrition, vol. 27, No. 1, Jul. 1998: 6–11.

Kim et al., *Does Laparoscopic vs. Conventional Surgery Increase Exfoliated Cancer Cells in the Peritoneal Cavity During Resection of Colorectal Cancer?* Dis Colon Rectum, vol. 41, No. 8, Aug. 1998:971–978.

Daltrey et al., *The Effect of Needle Gauge and Local anesthetic on the Diagnostic Accuracy of Breast Fine–needle Aspiration Cytology*, european Journal of Surgical Oncology, vol. 25, 1999: 30–33.

Petrelli et al., *Accuracy of Biopsy and Cytology for the Preoperative Diagnosis of Colorectal Adenocarcinoma*, Journal of Surgical Oncology, vol. 71, 1999: 46–49.

Balachandar et al., *Early Colorectal Cancer in a Flat Adenoma*, Journal of the National Medical Ass'n., vol. 91, No. 11, 1999:631–632.

Casco et al., *A New Device for Abrasive Cytology Sampling During Upper Gastrointestinal Endoscopy*, Endoscopy, vol. 31, 1999:348–351.

Thomson et al., *Are Endoscopic biopsies of Small Bowel as Good as Suction Biopsies for Diagnosis of Enteropathy?* Journal of Pediatric Gastroenterology and Nutrition, vol. 29, No. 4, Oct. 1999: 438–441.

Zweig et al., *Histopathology of Tissue Samples Removed Using the Microdebrider Technique*, American Journal of Rhinology, vol. 14, No. 1, Jan.–Feb. 2000: 27–32.

Brandborg et al., *Is Exfoliative Cytology Practical for more General Use in the diagnosis of Gastric Cancer?*, (Source not legible) 1960's: 1074–1080.

Cameron, *A Cytological Method of Diagnosis of Carcinoma of the Colon*, Thesis abridgement presented to Columbus Surgical Society, Columbus, OH, Jan. 1960: 230–236.

Cameron et al., *Recovery of Malignant Cells from Enema Returns in Carcinoma of the Colon*, Surgical Forum, undated:30–33.

Anonymous, *Summary of Safety and Effectiveness Data: AngioJet Rheolytic Thrombectomy System*, (undated), pp. 1–14.

Black et al., *Simple Method for Polyp Retrieval During Colonoscopy*, Dis Colon Rectum, vol. 37, 1994, 949.

Anonymous, *Understanding the Importance of Tissue Pathology*, Internet www.prometheus–labs.com, Jan. 17, 2001: 3 pages.

Drasler et al., *A rheolytic system for percutaneous coronary and peripheral plaque removal*, Abstract, Angiology, vol. 42, No. 2, Feb. 1991: 90–98.

Anonymous, *Mucoid Specimens (Respiratory and Gastrointestinal Specimens)*, Internet, www.cytyc.com, Jan. 17, 2001: 1 page.

Anonymous, *Cytorich Preservatives*, Internet www.tripathimaging.com, Jan. 17, 2001, 1 page.

Green et al.; *The Use of Gastric Salvage Cytology in the Diagnosis of Malignancy: A Review of 731 Cases*; Diagn. Cytopathol. 1990;6:1–4.

Dabbs et al.; *Immunocytochemistry on the ThinPrep Processor*; Diagn. Cytopathol. 1997;17:388–392.

Linder; *Recent Advances in Thin–Layer Cytology*; Diagn. Cytopathol. 1998;18:24–32.

Lapen et al.; *Performance Optimization of the ThinPrep Processor: Effect of Microscope Slides*; Diagn. Cytopathol. 1998; 19:388–391.

Gary et al.; *Cell Block Preparation on Residual ThinPrep Sample*; Diagn. Cytopathol. 1999;21:427–431.

Kochhar et al.; *Crush Preparations of Gastroesophageal Biopsy Specimens in the Diagnosis of Malignancy*; Acta Cytologica 1990 vol. 34 No. 2; pp. 214–216.

Darragh et al.; *Comparison of Conventional Cytologic Smears and ThinPrep Preparations from the Anal Canal*; Acta Cytologica 1997 vol. 41 No. 4; pp. 1167–1170.

Ferguson et al.; *Quantitative Analysis of MicrodebridersUsed in Endoscopic Sinus Surgery*; American Journal of Otolaryngology, 1999, vol. 20 No. 5: pp. 294–297.

Ehya et al.; *Crush Cytology in the Diagnosis of Colonic Neoplasms*; Cancer; Oct. 1, 1990; vol. 66, pp. 1563–1567.

McGarry et al.; *The effect of microdebriders on tissue for histological diagnosis*; Clin. Otolaryngol. 1997; vol. 22, pp. 375–376.

Green et al.; *Diagnosis of Metastatic Lesions to the Stomach by Salvage Cytology: A Report of Three Cases*; Digestive Diseases and Sciences, vol. 35, No. 11(Nov. 1990), pp. 1421–1425.

Brandborg et al.; *A Multipurpose Tube for Suction Biopsy*; Gastroenterology, vol. 37, No. 1(Jul. 1959), pp. 1–16.

Brandborg et al.; *"Low" versus "High" Concentration Chymotrypsin in Gastric Exfoliative Cytology*; Gastroenterology, vol. 57, No. 5 (Nov. 1969), pp. 500–505.

Graham et al.; *Salvage Cytology*; Gastrointestinal Endoscopy, vol. 25, No. 4(1979), pp. 137–139.

Graham et al.; *Endoscopic Needle Biopsy: A comparative studyof forceps biopsy, two different types of needles, and salvage cytology in gastrointestinal cancer*; Gastrointestinal Endoscopy, vol. 35, No. 3(1989), pp. 207–209.

Woods et al.; *Influence of endoscopic biopsy forceps charavteristics on tissue specimens: results of a prospective randomized study*; Gastrointestinal Endoscopy, vol. 49, No. 2(1999), pp. 177–183.

Maksem; *Cost–effective liquid–fixed cytology specimen processing with an economical cytocentrifuge*; Autocyte Inc., Clinical Note dtd Apr. 2000, pp. 8–9.

Watanabe et al.; *Diagnosis of Early Cancer of the Colon and Rectum*; Tohoku (Japan) Jour. of Experimental Medicine; 1979; vol. 129; pp. 183–195.

Standards of Practice Committee, American Society for Gastrointestinal Endoscopy; *Tissue Sampling and Analysis*; ASGE Publication 1025 4/91 (6 pages) Internet Publication: www.sages.org/sg_asgepub1025.html (Printed Apr. 13, 2000).

McGarry; *The re–dedication of microdebriders for rhinological surgery*; Clinical Forum, Audiology Feature 6–3, (8 pages) Internet Publication: http://ent–news.com/vol6_3/forum.dir/forum.html (Printed Apr. 27, 2000).

TriPath Imaging Inc.; *The PREP System*; (3 pages) Internet Publication: http://www.tripathimaging.com/prep.htm (Printed May 23, 2000).

* cited by examiner

FLUID-JET CATHETER AND ITS APPLICATION TO FLEXIBLE ENDOSCOPY

BACKGROUND OF THE INVENTION

Colorectal carcinoma is a leading cause of morbidity and mortality across the globe. Gastric carcinoma also is a leading concern worldwide. Colonoscopy is the most accurate screening tool for colorectal cancer, and an esophagogastroduodenoscopy is the preferred method for gastric screening. The means by which a diagnosis is made during endoscopy is in question, however. Many techniques of mucosal sampling have been utilized since Hemmeter in 1889 described an abrasive instrument for diagnosing gastric carcinoma. For example, pinch, snare, brush, suction, salvage and fine needle aspiration (FNA) are established sampling techniques for gastrointestinal endoscopy. Lavage cytology is now considered obsolete, but was the technique that cultivated major advances in gastrointestinal cytology. Brush, suction, salvage, and FNA deliver samples appropriate for cyto-analysis and their interpretation rest upon cytology data gleaned for over 100 years. Their practical use, however, is limited because of the time and effort required for completion. Histology samples delivered by pinch and snare techniques, although the more commonly performed because of their rapid results are flawed techniques with lower diagnostic yields than brush, suction and salvage techniques.

Needs exist for a novel means used during endoscopy that dissects tissue into a cellular suspension capable of undergoing analytical cytology.

SUMMARY OF THE INVENTION

Fluid jet tubes having operative openings and cell traps for cell cluster, tissue and debris harvesting and collecting are used in diagnostics and therapeutics. Used with an endoscope the fluid jets draw-in, stabilize and hold in vivo target specimens at a distal end. While the catheter grips the tissue by suction, blasts of high pressure saline solution strip from the tissue and suspend clusters of cells which are ready for analysis. The clusters of cells are entrained in the saline solution and are recovered in a cell collection trap at the proximal end. Traps are removed and replaced or rotated out of and into alignment with a trap connector to accommodate new target specimens.

A foot switch controls fluid flow and intensity and frequency of the fluid jet blasts of the saline solution. The fluid jet catheter paired with a fiber optic system in an endoscope allows viewing of the area immediately surrounding the distal end of the catheter.

In diagnostics the tubes and traps are used with flexible and rigid endoscopes. In the therapeutics the tubes and trap are used with rigid endoscopes and in free standing applications to collect cell cluster, tissue and debris samples from arterial thrombectomy, external biopsy, wound debriedment, surgical incisions and surgical excisions.

In one embodiment the present invention uses a flexible endoscope which stabilizes and holds in vivo target specimens at a proximal end. While the endoscope grips the tissue by suction, blasts of high pressure saline solution strip the tissue samples and break the tissue into suspended cells which are ready for analysis.

A fluid-jet catheter of the invention unites the advantageous qualities of conventional techniques into one swift technique allowing for results while consuming fewer resources.

This invention provides a flexible fluid-jet catheter capable of dissecting tissue into a cellular suspension for undergoing analytical cytology. Analytical cytology is a practical and effective approach to medical diagnosis.

The fluid-jet catheter of the present invention uses high velocity saline jets to create a Bernoulli effect for entrapment, dissection and retrieval of tissue cells, providing a novel approach for the diagnosis and treatment of pathology through the flexible endoscope. It fosters new initiatives in tumor diagnosis and management of lesions found by flexible endoscopy.

In other embodiments of the invention cell traps are provided on return lines of abrading and cutting fluid jets used for arterial thrombectomy, external and internal biopsies, wound debriedment and surgical incisions and excisions to collect cell clusters for further analyzing without further preparation.

High pressure fluid-jets have been successfully used in other medical devices. They have been used to create incisions during surgery, and to clean trauma wounds. The fluid-jet's application to flexible endoscopy, and specifically for the diagnosis and management of flexible endoscopic pathology has yet to be determined, however.

The fluid-jet dissects tissue into a cellular suspension capable of undergoing analytical cytology. Because of this, diagnostic rates are improved, and, unlike more commonly performed techniques, samples may be analyzed in-vitro with highly specific and sophisticated adjunctive techniques. A greater number of endoscopic lesions are capable of being diagnosed in cellular suspensions rather than permanently fixed in formalin. Eventually, such a rapid system for tissue sampling may stimulate improved techniques for point-of-care, on-site diagnosis. It may also stimulate new treatment modalities for endoscopic pathology in less invasive and more effective ways. It provides a novel means for less invasive treatment of conditions such as Polyposis coli and Barrett's esophagus.

The fluid-jet of the present invention is capable of being adjusted to various pulsation frequencies, pressures, patterns, fluid compositions, spray patterns and flow rates. In addition, the fluid-jet may be of any size. The fluid-jet provides means for retrieval of cell clusters from freshly dissected tissue. The retrieved tissue is immersed in a cytopreservative for transport of tissue freshly dissected by a fluid-jet.

Ideally, a limited range of fluid-jet settings would allow the dissection of many different tissue types into single cells, however, a wide variety of fluid-jet settings are available for dissecting different types of tissues.

The high pressure saline jet of a fluid-jet catheter may be of a single coherent stream, or may be of many geometric styles. Regardless of the pattern, the high velocity saline jet produces an immediate region of reduced pressure. Tissue is drawn into the path of the saline jet, and dissected free in the form of cell clusters. The cell clusters are then retrieved outside the flexible endoscope. The size of the fluid-jet orifice may also influence the effectiveness of the retrieval tube. The delivered cell clusters may then be re-suspended in a liquid based cytopreservative and prepared for analytical cytology.

Liquid-based analytical cytology is better than using fixed specimens because liquid-based cytology allows for conventional cyto-analysis of the cell clusters, thus allowing advanced adjunctive screening, such as flow cytometry and immunochemistry. Cell clusters may be examined with monoclonal or polyclonal antibodies to detect viral antigens of CMV, HSV and varicella zoster virus. In situ DNA or RNA hybridization using the polymerase chain reaction could also be used to detect the presence of viral DNA or RNA. These tests are rarely used in conventional sampling techniques because of the difficulty in obtaining an adequate sample. Once a sample is fixed in formalin, as are most endoscopic samples, analysis is limited. Current trends of endoscopic diagnosis seem primitive when compared to the tremendous data potentially gleaned from liquid-based cell suspensions.

Flexible endoscopes usually have at least one lumen employed for the management of endoscopic pathology. The fluid-jet catheter of the present invention uses the same lumen as do other techniques. Likewise, to sample an area of interest, the end piece of the fluid-jet catheter is positioned the same way as other techniques. With a foot switch, a high velocity saline jet is activated, and the corresponding cell clusters are delivered to a cell trap. The cell trap is removed, and the sample is re-suspended in a cytopreservative. The cell trap is replaced, but the fluid-jet catheter need not be removed from the endoscope port, unlike current techniques. The system is then ready for another session. The entire process should take less than ten seconds, a savings of over one minute per biopsy. This means the patient is under anesthesia up to fifteen-minutes less for ten biopsies taken during a procedure.

In addition to shorter biopsy times, there are several other therapeutic benefits to using fluid-jet catheters. Since a fluid-jet catheter could decrease the amount of time to remove diseased tissue, it may foster new initiatives in less invasive treatments. Conditions such as Polyposis coli, obstructive esophageal tumors, herniated disks, and gynecological tumors may take less time to treat using the fluid-jet endoscope catheter.

The dissected tissue may be captured in bridal crinoline, a 100% nylon fabric that is compatible with liquid-based cytology. The filtered cell clusters are then washed and re-suspended in a cytopreservative. Thin layer cytology slides are prepared using either an automated cell preparation station or a cyto-centrifuge, and are stained with Hematoxylin and Eosin. The slides may be visually inspected under a microscope.

A preferred embodiment of the fluid-jet catheter of the present invention is preferably at least five feet long, and less than 3.0 mm in outside diameter. The methods used to deliver the dissected tissue from the tip of the fluid-jet to the proximal end of the catheter involve either a positive pressure principle from the fluid-jet, or a negative pressure principle from wall suction. The fluid-jet is capable of exerting up to 20,000 psi. Ideally, the positive pressure generated from the high pressure fluid-jet will be such that the cell clusters are effectively pushed into and out of the retrieval tube.

Cytopreservatives are used to enhance the long term stability of cells dissected from tissue by fluid-jet. For example, hog intestinal mucosa remain well preserved in Cytorich red®, a slightly hemolytic cytopreservative, for several hours. Eventual, practical, widespread use of a fluid-jet endoscopic catheter will require the cell suspension to be stable for cytoanalysis for at least one week. Several commercially available cytopreservatives may be used and compared in their efficacy of preservation for up to one month. Fluid-jet dissection of tissue may have no untoward effects upon the cell suspension, or perhaps one cytopreservative is more effective than others.

These and further and other objects and features of the invention are apparent in the disclosure, which includes the above and ongoing written specification, with the claims and the drawings.

DETAILED DESCRIPTION OF THE PREFERRED EMBODIMENTS

The fluid-jet catheter of the present invention uses high velocity saline jets to create a low pressure Bernoulli effect for tissue entrapment, dissection by high speed jets, and retrieval of targeted tissue cells, providing a novel approach for the diagnosis and treatment of pathology using a flexible catheter endoscope.

Figure 2:
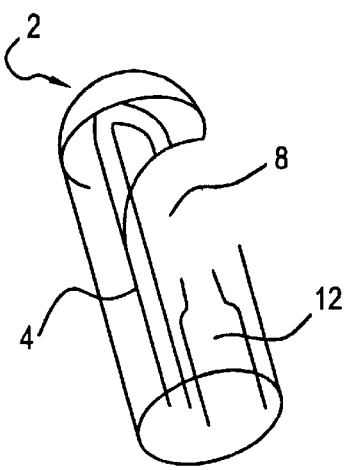
FIG. 2 is a perspective view of the end piece of the fluid-jet catheter of the present invention.
Figure 3:
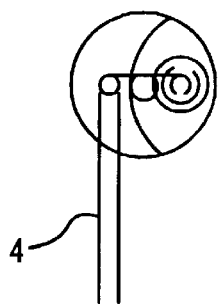
FIG. 3 is a detail view of the chamber within the end piece of the fluid jet catheter.

Flexible endoscopes usually have at least one lumen employed for the management of endoscopic pathology. The fluid-jet catheter of the present invention uses the same port as do other techniques, and extends from the proximal end to the distal end of the catheter within the lumen. To sample an area of interest, the end piece 2 of the fluid-jet catheter, shown in FIGS. 1–3, is positioned the same way as other techniques.

The fluid-jet provides means for retrieval of cell clusters from freshly dissected tissue. The retrieved tissue may be immersed in a cytopreservative for transporting tissue freshly dissected by a fluid-jet. The fluid-jet catheter of the present invention dissects tissue into a cellular suspension which is capable of undergoing analytical cytology.

The fluid-jet catheter of the present invention is preferably at least five feet long, and less than 3.0 mm in outside diameter. The methods used to deliver the dissected tissue from the distal end to the proximal end of the catheter involve either a positive pressure principle from the fluid-jet, or a negative pressure principle from wall suction. The fluid-jet is capable of exerting up to 20,000 psi.

Figure 1:
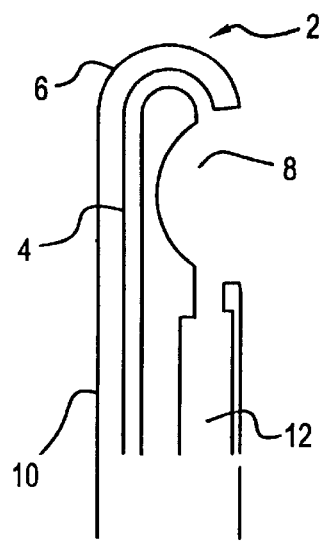
FIG. 1 is a cross-section view of the end piece of the fluid-jet catheter of the present invention.

FIG. 1 shows a cross-section view of an end piece 2 of a preferred embodiment of the fluid-jet catheter of the present invention. Preferably, the end piece 2 is constructed of stainless steel, but other materials may be used. In a preferred embodiment, the end piece 2 is cylindrical in shape with a domed top 6. However, the end piece 2 may be of any shape.

The end piece 2 incorporates a hollow chamber 4 through which the saline solution fluid jet flows. Preferably, the chamber 4 is cylindrical in shape, however, the chamber may be of any geometry. The chamber 4 extends partially through the end piece 2, interconnects outward flow tube and the return tube, and connects to a flow reverser 7 which redirects the flow of saline solution back towards the proximal end of the catheter. A lateral opening 8 is formed in an external side of the end piece 2. As saline solution is jetted through the chamber toward the distal or proximal end of the fluid-jet catheter, negative pressure in the chamber and opening is caused by saline solution jetting through the chamber past the lateral opening 8. Creating a Bernoulli effect causes suction, which allows targeted tissue to be drawn into the lateral opening 8 of the end piece 2. The surface of the inward-drawn tissue is abraded by the jet stream of saline solution which strips clusters of cells from the tissue. The clusters of cells are entrained in the saline solution and flow through a cell trap recovery opening 12 which decreases diameter in a downstream direction toward the proximal end of the catheter.

FIG. 2 is a perspective view of the end piece 2 of the fluid-jet catheter of the present invention, showing the spatial relationships between the chamber 4, the lateral opening 8 and the cell recovery opening 12. The chamber 4 of the end piece 2 is shown in detail in FIG. 3.

Figure 4:
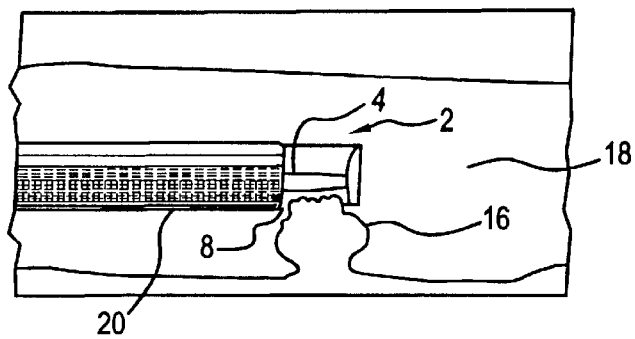
FIG. 4 shows the fluid-jet catheter of the present invention dissecting a polyp inside an intestine.
Figure 5A:
FIG. 5A is a cross-section view of the distal end of the fluid-jet catheter of the present invention.
Figure 5B:
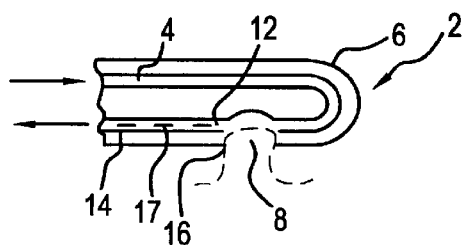
FIG. 5B is a cross-section view of the end piece of the fluid-jet catheter of the present invention.

FIG. 4 shows a schematic view of the fluid-jet catheter of the present invention dissecting cells from a polyp 16 inside of a colon 18. A targeted piece of the polyp 16 is drawn up into the lateral opening 8 of the end piece 2 due to suction created by a Bernoulli effect. As shown in FIGS. 5A and 5B, clusters 17 of cells are dissected from the polyp 16 by saline solution fluid jets pumped through the chamber 4 which extends through the end piece. Clusters of cells dissected from the tissue are then directed through a cell recovery opening and into a cell recovery tube which leads to a cell cluster trap.

FIGS. 5A and 5B are cross-section views of the dissecting distal end of the fluid-jet catheter of the present invention. FIG. 5A shows flexible tubing material 20 surrounding optical fibers 22 which are used for illuminating and conveying images of immediate surroundings of the fluid-jet end piece 2 to a viewing screen. The flexible tubing material 20 also surrounds a catheter tube 26 which houses a pressure tube 28 and a cell recovery return tube 14.

FIG. 5B is a cross-section view of tissue from a polyp 16 being drawn into the lateral opening 8 of the end piece. The polyp 16 is abraded by saline jets which flow through a chamber 4. The saline jets remove clusters of cells 17 from the targeted polyp 16; the clusters of cells 17 are entrained in the saline solution and are pushed through a cell recovery return tube 14 for collection at the proximal end of the catheter.

Figure 6:
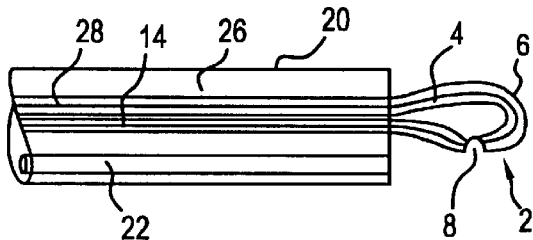
FIG. 6 is a cross-section view of the distal end of an alternative embodiment of the fluid-jet catheter of the present invention in which a wide end piece tapers to attach to the catheter tube.

FIG. 6 shows one embodiment of the fluid-jet catheter of the present invention in which the curve 6 of the end piece 2 has a larger diameter than the catheter tube 26, for smoothing flow and reducing pressure drop in the jetted fluid and allowing for dissection of large or irregularly shaped tissue samples. The end piece 2 tapers to attach to the catheter tube 26.

Figure 7:
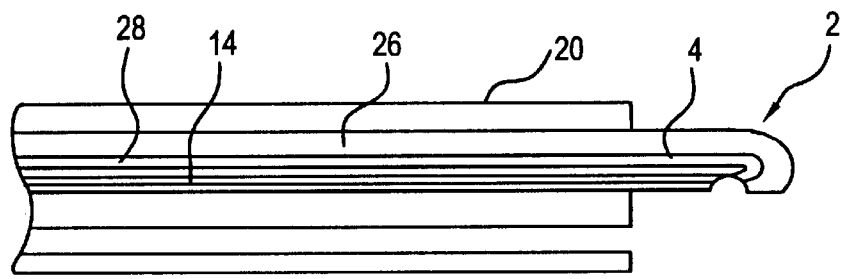
FIG. 7 is a cross-section view of the distal end of an alternative embodiment of the fluid-jet catheter of the present invention in which the pressure tube through which saline solution is pumped is concentric to the catheter tube.

FIG. 7 is a cross-section view of the dissecting, distal end of a preferred embodiment of the fluid-jet catheter of the present invention in which the pressure tube 28 through which saline solution is pumped into the chamber 4 extending through the end piece 2 is concentric with the catheter tube 26. The catheter tube 26 and optical fibers 22 are surrounded by flexible tubing material 20. A cell recovery tube 14 is housed within the catheter tube 26 for conveying dissected clusters of cells to the proximal end of the fluid-jet catheter of the present invention.

Figure 8:
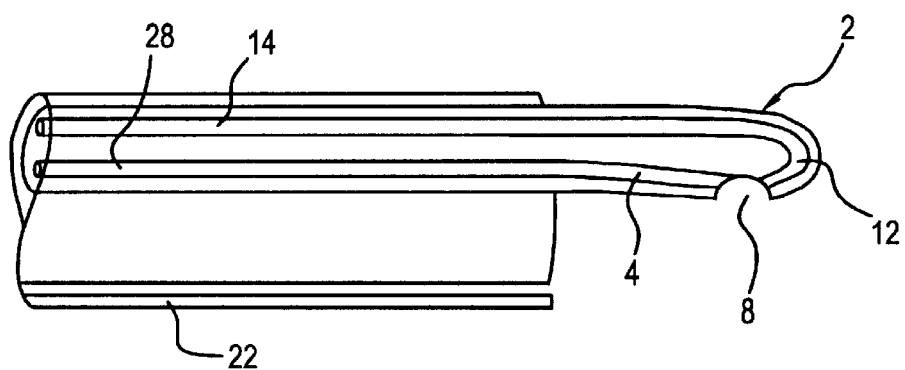
FIG. 8 is a cross-section view of an alternative embodiment of the fluid-jet catheter of the present invention in which saline solution is pumped through an opening in an end piece to create a reduced pressure.

FIG. 8 shows an alternative embodiment of the fluid jet catheter of the present invention. In this embodiment, the pressure tube 28 through which saline is pumped leads to a chamber 4 within an end piece 2 incorporating a lateral opening 8. The chamber 4 slopes toward the lateral opening 8, causing a Venturi effect, resulting in suction. Tissue is drawn up into the opening 8 and is contacted by a saline solution fluid jet. The fluid jet dissects clusters of cells from the tissue, which are then pumped through a cell recovery opening 12 in the end piece 2 and into the cell recovery tube 14 for conveyance to the proximal end of the fluid-jet catheter.

Figure 9:
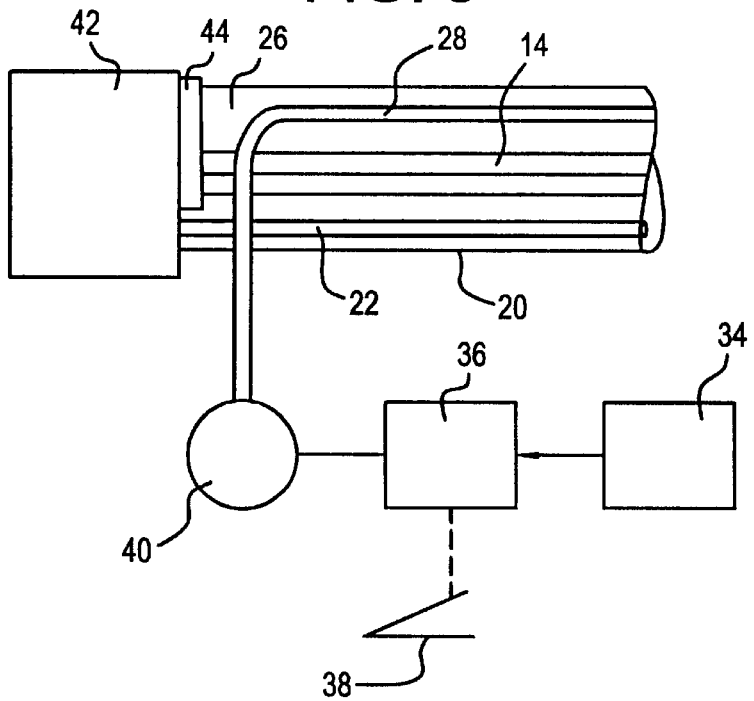
FIG. 9 is a schematic representation of the proximal end of the fluid-jet catheter of the present invention.

FIG. 9 is a schematic representation of the proximal end of the fluid-jet catheter of the present invention. A catheter tube 26 and optical fibers 22 are surrounded by flexible tubing material 20. Clusters of cells are passed through the cell recovery tube 14, which is housed within the catheter tube 26, and are deposited in a cell cluster trap 42 for storage and preservation. The cell cluster trap 42 is attached to the catheter tube by an attaching means 44 to facilitate removing and replacing the trap 42. A pressure tube 28 for pumping saline solution is housed within the catheter tube 26 and is connected to a pump 40. The pump is actuated by a controller 36, which may be attached to a foot switch 38. A power supply 34 supplies power to the controller 36 and to the pump 40.

A foot switch 38 may be used to govern the actuation of the pump 40 for generating a high velocity saline jet by pumping saline through a pressure tube 28. Targeted cell clusters contacted with the saline jet. The dissected targeted cells are then delivered to the proximal end of the fluid-jet catheter to a cell trap 42. The cell trap 42 is removed, and the sample may be resuspended in a cytopreservative. The cell trap 42 must be replaced, but the fluid-jet catheter tube 26 need not be removed from the endoscope port, unlike current techniques. The system is then ready for another session. The process may be accomplished quickly and should take less than ten seconds, a savings of over one minute per biopsy. This time savings is beneficial because a patient is under anesthesia up to fifteen-minutes less for ten biopsies taken during a procedure.

Figure 10:
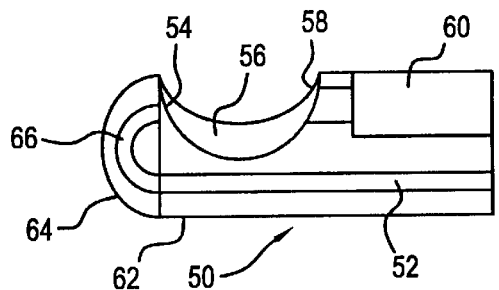
FIG. 10 shows a preferred catheter abraider or cutter tip.

Referring to FIG. 10, the fluid jet tip 50 used in diagnostics or therapeutics in conjunction with a cell trap. The tip 50 has a fluid jet lumen 52 which is curved to jet fluid from port 54 through operative opening 56 into receiver port 58 in the fluid return lumen 60. The jet tip 50 may be constructed of two molded parts. A body portion 62 contains the two lumens 52 and 60 and the operative opening 56. The end portion 64 contains the flow reversing curved portion 66 of high pressure lumen 52. The lumens may be in tubes confined in the tip structure. Preferably the lumens ports and operative opening are formed in the structure during molding.

Figure 11:
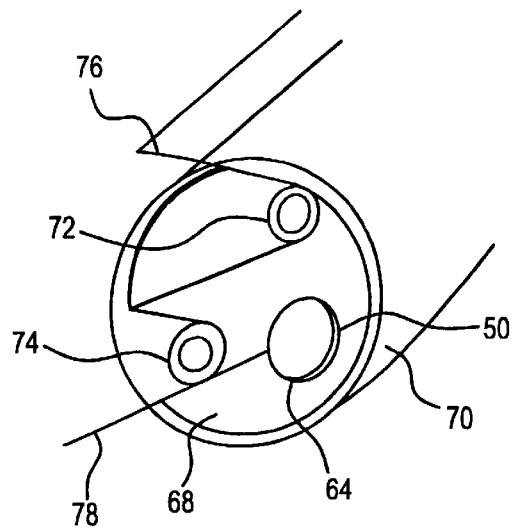
FIG. 11 schematically shows the illuminated end of an endoscope with the catheter ready to extend and sample a tissue.

FIG. 11 shows an end 68 of a lighted endoscope 70. Two fiber optic bundles 72 and 74 cast illumination 76 and 78 on internal targets within body organs and vessels through fibers in the bundles. The end 64 of the fluid jet tip 50 of a catheter may be fixed in the endoscope or more preferably may be slidable through the endoscope to make final adjustments for alignment of the tissue of interest with the operative opening in the tip 50.

Figure 12:
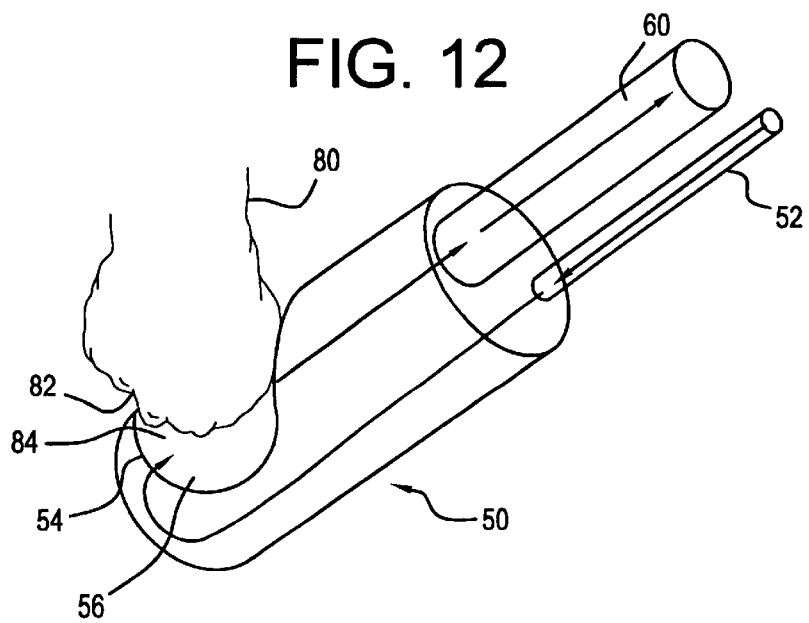
FIG. 12 schematically shows drawing a polyp into the operative opening and abraiding cell clusters from the polyp with fluid jets.

FIG. 12 shows the surface 82 of a polyp 80 being drawn into the operative opening 56 by negative pressure surrounding the jet 84 flowing across the opening from port 54 to port 58. Cell clusters are abraded from the polyp surface 82 and are entrained with the jetted fluid in the return lumen 60.

Flow through the tubes may be continuous, pulsed or intermittent. The return tube may have a larger diameter than the outward tube, to promote the jetting flow through the chamber. Suction, such as by aspiration, may be applied to the return tube downstream of the cell trap. The operator may, upon locating a polyp of interest, apply the aspiration or a lower outward flow or both to create a suction in the chamber. When observations through a screen attached to the fiber optic system, meters or alerts show that the tissue has been partially drawn into the chamber, the operator may further depress the pedal to increase or pulse the outward flow and maintain or increase the suction to abrade and collect cell clusters from the investigated polyp or tissue. The portion of the end is mapped. The flow is stopped, the cell trap is removed and marked to relate it to the mapped portion.

The distal end is moved to a new location while using the display screen. A new cell trap is inserted at the proximal end, and the cell cluster collection process is repeated. Many polyps or other tissue samples may be recovered without a lengthy process of withdrawing and reinserting a catheter.

A limited range of fluid-jet settings allows the dissection of many different tissue types into single cells or clusters of cells, however, a wide variety of fluid-jet settings are available for dissecting different types of tissues. The fluid-jet is capable of being adjusted to various pulsation frequencies, pressures, patterns, fluid compositions, spray patterns and flow rates. Preferably the fluid-jet is a saline solution fluid-jet. In addition, the fluid-jet may be of any size, as the size of the fluid-jet orifice may influence the effectiveness of dissection.

The high pressure saline jet of the fluid-jet catheter of the present invention may be of a single coherent stream, or may be of many geometric styles. Regardless of the pattern, the high velocity saline jet produces an immediate region of reduced pressure. Because of this region of reduced pressure, tissue is drawn into the path of the saline jet, and cell clusters are dissected free from the targeted tissue. The cell clusters are then retrieved outside the catheter. The delivered cell clusters may then be re-suspended in a liquid based cytopreservative and prepared for analytical cytology.

Liquid-based analytical cytology is better than using fixed specimens because liquid-based cytology allows for conventional cyto-analysis of the cell clusters, thus allowing advanced adjunctive screening, such as flow cytometry and immunochemistry. Cell clusters may be examined with monoclonal or polyclonal antibodies to detect viral antigens of CMV, HSV and varicella zoster virus. In situ DNA or RNA hybridization using the polymerase chain reaction could also be used to detect the presence of viral DNA or RNA.

The dissected clusters of cells collected in the cell cluster trap by the fluid-jet catheter of the present invention may be captured in bridal crinoline, a 100% nylon fabric that is compatible with liquid-based cytology. The filtered cell clusters may then be washed and re-suspended in a cyto-preservative. Thin layer cytology slides may be prepared using either an automated cell preparation station or a cyto-centrifuge, and may be stained with Hematoxylin and Eosin or other prepared stains. The slides may be visually inspected under a microscope or subjected to other types of analysis.

Cytopreservatives may be used to enhance the long term stability of cells dissected from tissue by fluid-jet catheter of the present invention. For example, hog intestinal mucosa remain well preserved in Cytorich red®, a slightly hemolytic cytopreservative, for several hours. Eventual, practical, widespread use of a fluid-jet endoscopic catheter will require the cell suspension to be stable for cytoanalysis for at least one week. Several commercially available cytopreservatives may be used and compared in their efficacy of preservation of clusters of cells for up to one month. Fluid-jet dissection of tissue may have no untoward effects upon the cell suspension, or perhaps one cytopreservative is more effective than others.

While the invention has been described with reference to specific embodiments, modifications and variations of the invention may be constructed without departing from the scope of the invention, which is defined in the following claims.

I claim:

1. Sample collection apparatus comprising a catheter having a proximal and a distal end, a pressure tube connected to the catheter and extending from the proximal to the distal end of the catheter, a cell recovery tube connected to the catheter and extending from the proximal to the distal end of the catheter, and a cell cluster trap connected to the cell recovery tube at the proximal end of the catheter for obtaining, dissecting and storing dissected tissue samples from targeted tissue within a body and conveying the dissected tissue samples from the body.

2. The apparatus of claim 1, further comprising an operator connected at the proximal end of the catheter and a flow reverser connected to at least one of the pressure tube and the cell recovery tube at a distal end of the catheter.

3. The apparatus of claim 2, wherein the operator is a handpiece.

4. The apparatus of claim 3, further comprising a connector for connecting the cell cluster trap to the handpiece.

5. The apparatus of claim 1, further comprising a chamber with a lateral aperture connected between the pressure tube and the cell recovery tube at the distal end of the catheter.

6. The apparatus of claim 5, further comprising a flow reverser connected to the chamber and to at least one of the pressure tube and the cell recovery tube at a distal end of the catheter.

7. The apparatus of claim 6, wherein the flow reverser is connected to the chamber and the pressure tube at a distal end of the cell recovery tube.

8. The apparatus of claim 1, wherein the cell cluster trap is detachable from the cell recovery tube.

9. The apparatus of claim 1, further comprising plural cell cluster traps for sequentially attaching and removing from the catheter.

10. The apparatus of claim 1, further comprising an endoscope having a proximal end and a distal end and having a lumen extending from the proximal end to the distal end of the endoscope for receiving the catheter in the lumen.

11. The apparatus of claim 10, further comprising optical fibers disposed in the endoscope and extending from the proximal end to the distal end of the endoscope, a light source connected to at least one of the optical fibers at the proximal end of the endoscope for illuminating a body at the distal end of the endoscope.

12. The apparatus of claim 11, further comprising a viewing screen connected to at least on of the optical fibers for projecting an image of a view surrounding the distal end of the catheter.

13. The apparatus of claim 12, further comprising a pressure source connected to a proximal end of the pressure tube, a suction source connected to a proximal end of the cell recovery tube, a power source connected to the pressure source and the suction source and a foot switch control connected to the power source for starting the sources and then intensifying the sources when a tissue to be sampled is adjacent the distal end as seen in the viewing screen.

14. Sample collecting apparatus comprising a catheter tube, a pressure tube within the catheter tube, a pump connected to the pressure tube for pumping saline solution through the pressure tube, a saline solution source connected to the pump, an end piece having a flow reverser attached to a distal end of the catheter tube for redirecting flow of saline solution and having a lateral opening for attracting the targeted tissue into the lateral opening and for dissecting clusters of cells from the targeted tissue, a cell recovery tube connected to the end piece for transporting the dissected clusters of cells, a cell cluster trap connected to a proximal end of the cell recovery tube for collecting and storing the clusters of cells, a controller connected to the pump for controlling actuation of the pump, and a power supply connected to the pump and to the controller for supplying power to the pump for obtaining, dissecting and storing clusters of cells from within a body.

15. The apparatus of claim 14, further comprising a foot switch connected to the controller for governing the actuation of the controller.

16. The apparatus of claim 14, further comprising an opening connected between the lateral opening and the cell recovery tube for directing saline solution and the clusters of cells into the cell recovery tube.

17. The apparatus of claim 14, further comprising a connecting means connecting the cell recovery tube to the cell cluster trap for facilitating removal and replacement of the cell cluster trap.

18. A sample collection method comprising obtaining, dissecting and storing clusters of cells from targeted tissue by inserting a catheter in a body, transmitting fluid pressure through the catheter, drawing tissue partially into a chamber and partially dissecting the tissue and forming clusters of cells, entraining the clusters of cells through the catheter to a cell cluster trap and storing the clusters of cells in the cell cluster trap.

19. The method of claim 18, wherein the transmitting fluid pressure further comprises adjusting pulsation frequency, pressure, spray pattern, fluid composition and flow rate of a saline solution.

20. The method of claim 18, further comprising using a foot switch to govern the actuation of the controller.

21. The method of claim 18, wherein the applying fluid pressure comprises pumping a saline solution at pressures up to 20,000 psi.

22. The method of claim 18, wherein the inserting a catheter in a body is controlled by a human.

23. The method of claim 18, wherein the inserting a catheter in a body is controlled by a machine.

24. The method of claim 18, further comprising contacting the clusters of cells with a cytopreservative.

25. The method of claim 18, further comprising sequentially removing and replacing the cell cluster trap.

26. Diagnostic or therapeutic fluid jet applicator apparatus comprising a tubular structure having distal and proximal ends first and second lumens extending between the ends of the tubular structure, the first and second lumens having proximal ends near the proximal end of the tubular structure and having distal ends near the distal end of the tubular structure, an operative opening between the lumens at the distal end of the tubular structure, a pressure source connection at the proximal end of the tubular structure for connecting the pressure source to the proximal end of the first lumen, a cell trap connection at the proximal end of the tubular structure for connecting a cell trap to the proximal end of the second lumen, a drain connection at the proximal end of the tubular structure for removing fluids from the proximal end of the second lumen.

27. The apparatus of claim 26, wherein the operative opening comprises an opening for drawing abraded material into a distal end of the second lumen.

28. The apparatus of claim 26, wherein the cell trap connection further comprises multiple connections for sequentially connecting multiple cell traps to the proximal end of the second lumen.

29. The apparatus of claim 26, wherein the operative opening at the distal end of the tube enables arterial thrombectomy.

30. The apparatus of claim 26, wherein the operative opening at the distal end of the tube enables internal biopsy.

31. The apparatus of claim 26, wherein the tube comprises a flexible catheter.

32. The apparatus of claim 31, wherein the flexible catheter is disposed in a flexible endoscope with fiber optics for viewing an environment of the endoscope and the tube at the distal end.

33. The apparatus of claim 26, wherein the tube is rigid and wherein the rigid tube is disposed in an operative opening at the end of the tube.

34. The apparatus of claim 26, wherein the distal operative opening at the end of the tube is used for external biopsy, wound debriedment, surgical incisions or surgical excisions.

35. The apparatus of claim 26, further comprising a cell trap removably connected to the cell trap connector.

36. The apparatus of claim 26, further comprising multiple cell traps connected to a cell trap mount for sequentially connecting each cell trap to the proximal end of the second lumen.

37. The apparatus of claim 35, wherein the operative opening comprise an opening for exposing tissue to a fluid jet from a distal end of the first lumen.

38. The apparatus of claim 26, further comprising a pump connected to the pressure source connection and a controller connected to the pump.

39. The apparatus of claim 26, wherein the tubular structure comprises first and second tubes respectively having the first and second lumens.

40. The apparatus of claim 26, wherein the tubular structure comprises a single tube having first and second lumens therein.

41. A diagnostic or therapeutic method comprising directing fluid jets to a tissue, abrading the tissue, entraining cell clusters from the abraded tissue in a fluid and conveying cell clusters in the fluid, trapping cell clusters from the fluid and discharging the fluid.

42. The method of claim 41 wherein the directing further comprises pumping fluid through a first tube and jetting fluid from the first tube toward an opening in a second tube and drawing tissue toward the jetting fluid.

43. The method of claim 42 wherein the entraining comprises entraining the cell clusters into the opening in the second tube.

44. The method of claim 43 wherein the trapping comprises receiving cell clusters in a trap and further comprising removing and replacing the trap with another trap.

* * * * *